United States Patent [19]
Roux et al.

[11] 3,985,892

[45] *Oct. 12, 1976

[54] PHARMACEUTICAL PREPARATION FOR PERCUTANEOUS TREATMENT OF LOCAL EDEMAS EMPLOYING ACETAZOLAMIDE

[75] Inventors: Claude P. Roux, Paris; Dieran Robert Torossian, Montrouge, both of France

[73] Assignee: Jouveinal S.A., Val de Marne, France

[ * ] Notice: The portion of the term of this patent subsequent to Jan. 20, 1993, has been disclaimed.

[22] Filed: Jan. 27, 1975

[21] Appl. No.: 544,039

Related U.S. Application Data

[63] Continuation-in-part of Ser. No. 146,298, May 24, 1971, Pat. No. 3,934,016.

[52] U.S. Cl. .............................................. 424/270
[51] Int. Cl.² ...................................... A61K 31/425
[58] Field of Search .................................. 424/270

[56] References Cited
OTHER PUBLICATIONS

Remingtons Pharmaceutical Sciences, 13th Ed. (1965), pp. 884, 1016–1017, 1240, 1424–1426.

*Primary Examiner*—V. D. Turner
*Attorney, Agent, or Firm*—Charles E. Baxley

[57] ABSTRACT

Method for percutaneous treatment of edemas of humans to reduce their swelling, by percutaneous application of a pharmaceutical preparation comprising an active element consisting of acetazolamide in a concentration of between 1 to 50% incorporated in a vehicle which is compatible with percutaneous administration.

4 Claims, No Drawings

PHARMACEUTICAL PREPARATION FOR PERCUTANEOUS TREATMENT OF LOCAL EDEMAS EMPLOYING ACETAZOLAMIDE

CROSS REFERENCE

This is a continuation-in-part application with respect to our copending United States Patent Application 146,298 filed May 24, 1971, now U.S. Pat. No. 3,934,016.

BACKGROUND OF THE INVENTION

The present invention relates to an improvement in therapeutic means employed for treatment of localized edemas of humans. More particularly the invention concerns percutaneous use of acetazolamide and the advantages inherent in this manner of introducing the acetazolamide. It is generally recognized that use of a diuretic by mouth for treatment of localized edemas presents metabolic drawbacks such as modification of ionic equilibrium, without contributing any very definitive curative effect on the edema.

In the case of acetazolamide, oral administration causes substantial acidosis (determined by the decrease in the value of the alkaline reserve of the blood) as well as a loss of potassium (detected by the drop of the potassium content of the serum). A good improvement in the treatment would consist in increasing local therapeutic effects of acetazolamide on edemas and decreasing the harmful effects (acidosis and hyperkalemia).

BRIEF DESCRIPTION OF THE INVENTION

Applicants have found now that by administering acetazolamide percutaneously in the form of an ointment or cream one can reduce localized edemas without repercussion on blood constants.

1. First of all, it was discovered that acetazolamide, contrary to other diuretic molecules, has the property of passing through the epidermal barrier. This property can be shown by the following experiment (from Lipschitz et al., J. Pharm. Exp. Therap. 1943, 79, p. 97). Rats, divided into 3 homogeneous lots, were given an aqueous overload of 5% of their body weight by intraperitoneal injection of physiological salt solution. One control lot received merely an application of the vehicle of the ointment. A series of lots (rats) was treated by application of ointment containing 10% acetazolamide. A series of lots was treated by oral administration of acetazolamide.

| Series | % increase in diuresis at the end of 4 hr. | Probability |
|---|---|---|
| Acetazolamide per os in a dose of: | | |
| 2 mg/kg | 22% | 0.02 < p < 0.05 |
| 5 mg/kg | 33% | p < 0.001 |
| 10 mg/kg | 35% | p < 0.001 |
| 20 mg/kg | 48% | p < 0.001 |
| Acetazolamide in ointment in a dose of: | | |
| 10 mg/kg | 20% | not significant |
| 20 mg/kg | 33% | 0.01 < p < 0.02 |
| 100 mg/kg | 42% | p < 0.001 |

The same experiment, carried out by administering other diuretic products such as triamterene, spironolactone, mercaptomerine, theophylline, in ointment form, showed that these substances did not cause diuresis.

2. In the second step, it was sought to determine whether acetazolamide administered as an ointment could inhibit formation of a localized edema caused in an animal and in what dose. A method was used in which an edema of the paw of the rat was caused by injection of kaolin into the plantar aponeurosis. (Method of J. Millebrecht - Arzneimittel Forschung 1954, 4, 607). It was found that acetazolamide significantly opposes formation of edema, first, starting with a dose of 10 mg/kg in ointment form and second, starting with a dose of 50 mg/kg per os.

3. Thereupon the doses causing diuresis or a protective effect with respect to edema, in accordance with the two methods of administration, were compared. The following table is obtained:

| Method of administration | Dose in mg/kg as from which there is significantly observed: | |
|---|---|---|
| | A diuretic effect | An anti-edema effect |
| Per os | 2 | 50 |
| Percutaneous | 20 | 10 |

This table makes it possible to note that administration of acetazolamide, percutaneously, makes it possible to obtain antiedema effects in low dose, far before the diuretic effect.

4. It was then verified clinically that administration of acetazolamide in an ointment actually provided a suitable therapeutic effect without causing harmful secondary effects. For this purpose, two classes of patients having localized edemas were selected, namely:

a. Post-traumatic edemas,
b. Edemas of cellulitic type.

The acetazolamide was administered in the form of a 10% ointment and the results were classified as:

Very good: the measurements had become normal again, the pain had disappeared, perfect mobility of the joints.

Good: Persistence of a certain degree of edema not having any functional consequence, almost complete disappearance of pain.

Rather good: presence of a partial improvement of the edema with slight functional disturbance, attenuation of the pain with persistence of moderate disturbance.

Zero: failure or insufficient action leaving appreciable functional disturbance, inadequacy or absence of effect on the pain.

| | Total | Very Good | Good | Rather Good | Zero | % Very Good + Good |
|---|---|---|---|---|---|---|
| Post-traumatic edemas | 78 | 45 | 15 | 9 | 9 | 78 |

| | Total | Very Good | Good | Rather Good | Zero | % Very Good + Good |
|---|---|---|---|---|---|---|
| Cellulitic edemas | 92 | 25 | 39 | 12 | 16 | 70 |

The effects on the alkaline reserve and on the blood potassium were determined:
Alkaline reserve: 56 observations, all within normal values.
Ionogram: 30 observations, all within normal values.

5. It was verified clinically that administration of acetazolamide in an ointment gives therapeutic effects superior to administration by mouth. For this purpose, acetazolamide was administered in succession by one or the other method:
  in a first group of patients: 8 days by mouth and then 8 days locally,
  in a second group: 8 days locally and then 8 days by mouth.

This procedure is necessary in order to eliminate the spontaneous improvement of the edema which favors in particular the first form administered. The results were as follows:

| Average decrease of edema | Tablets | Ointment | Probability |
|---|---|---|---|
| Tablets before ointment | 0.68 | 0.77 | 10 < p < 50 |
| | Ointment | Tablets | |
| Ointment before tablets | 1.81 | 0.63 | 1 < p < 2 |

Therefore, the administration of ointment proves to be more effective than the administration of tablets, with the probability of 98 to 99%.

The present invention can be carried out by conventional methods, the acetazolamide being incorporated in vehicles compatible with percutaneous administration. Thus it can be presented in the form of a suspension or emulsion, leading to conventional presentations, such as lotions, milks, creams, ointments, etc. The acetazolamide concentration will be between 1 and 50% and will advantageously be established at 10%.

EXAMPLES

The following examples are given to permit a better understanding of the invention, without, however, limiting its scope:

| 1. Anhydrous ointment Formula | |
|---|---|
| acetazolamide | 10 |
| poly-oxy-ethylene glycol 1500 | 75 |
| poly-oxy-ethylene glycol 300 | 15 |

In a double-jacketed stainless steel vessel, melt the mixture of poly-oxy-ethylene glycols at 48° C. Slowly add the acetazolamide in very finely pulverized form, with agitation. Cool with agitation to about 20° C and distribute in suitable containers.

| 2. Skin Cream Formula | |
|---|---|
| acetazolamide | 10 |
| poly-oxy-ethylene glycerides | 10 |
| polyethylene glycol stearate 300 | 10 |
| preservatives | |
| methyl para-hydroxybenzoate | 0.07 |
| propyl para-hydroxybenzoate | 0.03 |
| water q.s.p. | 100 g |

In a stainless steel vessel, melt the mixture of poly-oxy-ethylene glycerides and polyethylene glycol stearate 300 at 38° C. The preservative, which is an anti-fungus and anti-microbic agent, may in particular be a mixture of methyl para-hydroxybenzoate and propyl parahydroxybenzoate. Add the finely pulverized acetazolamide. Stir until completely dispersed. Slowly add an aqueous solution of the preservative, brought to 38° C. Stir until homogeneous. Cool slowly to 20° C with agitation. Distribute into suitable receptacles.

| 3. Suspension for Use on the Skin Formula | |
|---|---|
| acetazolamide | 10 |
| polyethylene glycol stearate 300 | 10 |
| stearic acid | 5 |
| petrolatum oil | 3.5 |
| ascorbyl palmitate | 3 |
| water q.s.p. | 100 g |

In a stainless steel vessel, melt at 40° C the mixture of polyethylene glycol stearate 300, stearic acid and oil of petrolatum. Add the finely pulverized acetazolamide. Stir until completely dispersed. Slowly add anaqueous solution of the preservative, brought to 38° C. The preservative may in particular be ascorbyl palmitate. Stir until homogeneous. Cool slowly to 20° C with agitation. Distribute into suitable receptacles.

We claim:
1. A pharmaceutical composition for local external cutaneous treatment of a local subcutaneous edema of a human, the composition comprising a suspension for skin use consisting of the following:
  10 parts of acetazolamide (5-acetamido-1,3,4-thiadiazole-2-sulfonamide),
  10 parts of polyethylene glycol 300,
  5 parts of stearic acid,
  3.5 parts of liquid petrolatum,
  3 parts of ascorbyl palmitate and
  100 parts of water q.s.p.

2. A skin cream for local external cutaneous treatment of a local subcutaneous edema of a human, the skin cream comprising:
  10 parts of acetazolamide (5-acetamido-1,3,4-thiadiazole-2-sulfonamide),
  10 parts of poly-oxy-ethylene glycerides,
  10 parts of polyethylene glycol stearate 300,
  0.07 parts of methyl para-hydroxybenzoate,
  0.04 parts of propyl para-hydroxybenzoate and
  100 parts of water q.s.p.

3. A method for cutaneous local treatment of a local subcutaneous edema of a human which method comprises applying to the skin over the edema a pharmaceutical composition which comprises:

a pharmaceutical carrier compatible with cutaneous external application, a diuretic agent capable of passing the epidermal barrier incorporated in the pharmaceutical carrier; said agent being acetazolamide (5-acetamido-1,3,4-thiadiazole -2-sulfonamide), with a range of concentration being between 1% and 50% by weight.

4. A method for cutaneous local treatment of a local subcutaneous edema of a human which method comprises applying to the skin over the edema a pharmaceutical composition which comprises:

an emulsified pharmaceutical carrier compatible with cutaneous external application, a diuretic agent capable of passing the epidermal barrier incorporated in the pharmaceutical carrier; said agent being acetazolamide (5-acetamido-1,3,4,-thiadiazole-2-sulfonamide), with a range of concentration being between 1 and 50% by weight.

* * * * *